United States Patent [19]

Yoshihara et al.

[11] Patent Number: 5,179,010
[45] Date of Patent: Jan. 12, 1993

[54] FERMENTATION PROCESS FOR PRODUCING L-LYSINE

[75] Inventors: Yasuhiko Yoshihara, Yokohama; Yoshio Kawahara, Kawasaki; Shigeho Ikeda, Yokohama, all of Japan

[73] Assignee: Ajinomoto Co., Inc., Tokyo, Japan

[21] Appl. No.: 469,687

[22] Filed: Jan. 26, 1990

Related U.S. Application Data

[63] Continuation of Ser. No. 870,825, Jun. 5, 1986, abandoned.

[30] Foreign Application Priority Data

Jun. 10, 1985 [JP] Japan .................... 60-125499

[51] Int. Cl.⁵ .................. C12P 13/08; C12N 1/20; C12N 1/38; C12N 1/00
[52] U.S. Cl. .................. 435/115; 435/252.1; 435/172.1; 435/843; 435/840; 435/244
[58] Field of Search .......... 435/115, 252.1, 172.1, 435/843, 840, 244

[56] References Cited

U.S. PATENT DOCUMENTS 3,929,571  12/1975  Kubota et al. .................. 435/115
4,529,697   7/1985  Yoshimura et al. ............. 435/110

OTHER PUBLICATIONS

Brock, T. D. "Biology of Microorganisms", Prentice Hall, 1979, p. 757.
Brock, T. D., "Biology of Microorganisms", 3rd ed, 1979, p. 288.
ATCC Catalog, 1985 pp. 39, 54, 55.
Goodfellow et al. "The Biology of Actinomycetes", 1985.

*Primary Examiner*—Irene Marx
*Attorney, Agent, or Firm*—Oblon, Spivak, McClelland, Maier & Neustadt

[57] ABSTRACT

A fermentative process for producing L-lysine is disclosed. The process is based on growing in a culture medium a mutant strain of the genus Brevibacterium or Corynebacterium (1) capable of producing L-lysine, and (2) having an intensified superoxide dismutase activity.

4 Claims, No Drawings

FERMENTATION PROCESS FOR PRODUCING L-LYSINE

This application is a continuation of application Ser. No. 870,825 filed on Jun. 5, 1986, now abandoned.

BACKGROUND OF THE INVENTION

1. Field of the Invention

This invention relates to the fermentative production of L-lysine. More particularly, it relates to a fermentation process for producing L-lysine by using a microorganism belonging to the genus Brevibacterium or Corynebacterium.

2. Discussion of the Background

A large number of methods have been proposed for producing L-lysine by fermentation processes. These include: the method of using strains resistant to S-(2-aminoethyl)-1-cysteine (hereinafter abbreviated as AEC) disclosed by Japanese Patent Publication No. 55213 (1967); the method of using mutant strains which are resistant to AEC, and are L-leucineless, L-homoserineless, L-prolineless, L-arginineless or L-alanineless (hereinafter referred to as Ala$^-$) disclosed by Japanese Patent Application Laid-open No. 36888 (1974), No. 80289 (1974) and No. 21078 (1976); the method of using mutant strains resistant to AEC and leucine analogues, such as β-hydroxyleucine (hereinafter abbreviated as HL) disclosed by Japanese Patent Publication No. 1833 (1978); the method of using mutant strains resistant to α-chlorocaprolactam (hereinafter abbreviated as CCL) disclosed by Japanese Patent Publication No. 43591 (1978); the method of using γ-methyllysine (hereinafter abbreviated as ML) disclosed by Japanese Patent Publication No. 19235 (1981); the method of using strains sensitive to fluoropyruvic acid (hereinafter abbreviated as FP) disclosed by Japanese Patent Application Laid-open No. 9783 (1980); and the method of using mutant strains with lowered pyruvic acid kinase activity disclosed by Japanese Patent Application Laid-open No. 170487 (1983).

All of these fermentative processes for producing L-lysine are expensive, making the L-lysine itself expensive. In view of the considerable demand on L-lysine there is therefore a strongly felt need for a more economical process for the production of L-lysine.

SUMMARY OF THE INVENTION

Accordingly, it is an object of this invention to provide a novel process for producing L-lysine.

It is another object of this invention to provide a novel process for the fermentative production of L-lysine.

It is another object of this invention to provide a novel and economical fermentative process for the production of L-lysine.

The inventors have now surprisingly discovered that the process of this invention satisfies all of the above objects and other objects which will become apparent from a reading of the description of the invention given herein below. This process is based on the inventors' discovery that by growing, in a liquid culture medium, a mutant strain belonging to the genus Brevibacterium or Corynebacterium, capable of producing L-lysine and having an intensified superoxide dismutase activity, L-lysine is very economically produced.

DETAILED DESCRIPTION OF THE PREFERRED EMBODIMENTS

Studies on strain improvement aimed at higher fermentation yields have led the present inventors to find that enhancing the superoxide dismutase activity of a L-lysine producing strain drastically enhances its L-lysine producing capacity. The present invention was accomplished based on these findings.

This invention thus relates to a new fermentation process for producing L-lysine. This process comprises growing, in a liquid culture medium, a mutant strain belonging to the genus Brevibacterium or Corynebacterium. The mutant strain used is capable of producing L-lysine and has an intensified superoxide dismutase activity. The L-lysine formed and accumulated in the liquid culture is then collected.

The microorganisms used in the process of this invention may be obtained by mutating a strain belonging to the genus Brevibacterium or Corynebacterium, capable of producing L-lysine and having an intensified superoxide dismutase activity. From the mutants thus obtained, those strains which are resistant to superoxide production accelerators, to superoxide dismutase induction inhibitors, to superoxide radical reaction accelerators, and to oxidizing agents that supply oxygen for the formation of superoxide, are selected and used. The mutant strains thus selected have intensified superoxide dismutase activity.

The mother strains from which the L-lysine producing strains used in this invention are derived may be any species belonging to the genus Brevibacterium or Corynebacterium. However, those which are known as coryneform, L-glutamic acid producing strains as enumerated below are particularly suitable.

| | |
|---|---|
| Brevibacterium divaricatum | ATCC 14020 |
| Brevibacterium flavum | ATCC 14067 |
| Brevibacterium lactofermentum | ATCC 13869 |
| Brevibacterium roseum | ATCC 13825 |
| Corynebacterium acetoacidophilum | ATCC 13870 |
| Corynebacterium lilium | ATCC 15990 |

These mutants, imparted with new properties advantageous for production of lysine (for example, resistance to AEC, CCL and ML, sensitivity to FP threonine and methionine, and homoserineless and Ala$^-$ properties) can be used.

Ultraviolet irradiation, X-ray irradiation, treatment with a mutagen, and any other techniques commonly used for mutation of microorganisms may be employed to derive the mutant strains of this invention from a Brevibacterium or Corynebacterium strain imparted with properties advantageous for lysine production. Treatment with 250 μg/ml of N-nitro-N'-methyl-N-nitrosoguanidine at 30° C. for 20 minutes is an example.

The next step is to select, from the variant cells thus produced, those strains which are resistant to superoxide production accelerators, superoxide dismutase induction inhibitors, superoxide radical reaction accelerators, or oxidizing agents that supply oxygen for the formation of superoxide. All of these agents have activity to accelerate the formation of peroxylipids by reaction between superoxide ($O_2^-$) and unsaturated fatty acids. To put it another way, the strains resistant to these agents must have high cell activity and would be able to actively propagate even under conditions that discourage cell activity. In fact, we have demonstrated that these are best suited for production of L-lysine.

The superoxide production accelerators are agents which accelerate production of superoxide in living bodies. These include methyl viologen, nitrofurantoin, vitamin $K_1$, morphine, streptonigrin, adriamycin, mitomycin C, daunomycin, bleomycin, $\beta$-rapacon, and cis-platinum(II) diamino dichloride.

The superoxide dismutase induction inhibitors are agents which inhibit the formation of superoxide dismutase in living bodies; an enzyme to convert superoxide to hydrogen peroxide. Puromycin is a typical example.

Superoxide radical reaction accelerators are agents which accelerate the formation of peroxylipids by reaction between superoxide and unsaturated fatty acids. Phenylhydrazine is a typical example.

The oxidizing agents are compounds which supply oxygen necessary for the formation of superoxide in living bodies, such as benzoyl peroxide and ammonium persulfate.

Strains resistant to these agents can be collected by any known technique commonly used to collect drug-resistant strains. For example, the variant cells obtained by mutation are spread on an agar medium containing any one of the above-mentioned agents in an amount that arrests the growth of the mother strain. The colonies which develop are collected. The suitable concentration of agent in the agar medium differs depending on the type of agent; but about 1.5 $\mu$g/ml for methyl viologen, about 0.5 $\mu$g/ml for puromycin, about 20 $\mu$g/ml for phenylhydrazine, and about 20 $\mu$g/ml for benzoyl peroxide are suitable. For others, the suitable concentrations should be determined by preliminary tests.

Alternatively, the mutant strains of this invention having greatly enhanced lysine productivity can also be obtained by first mutating a natural strain of Brevibacterium or Corynebacterium. From the mutants thus produced, those strains which are resistant to superoxide production accelerators, superoxide dismutase induction inhibitors, superoxide radical reaction accelerators, or oxidizing agents that supply oxygen for the formation of superoxide are selected. Finally the resistant strains thus selected are imparted with properties advantageous for lysine formation, such as resistance to AEC, CCL and ML, homoserineless property, and sensitivity to FP.

Illustrative examples of the microorganisms that can be used in the process of this invention include, among others, *Brevibacterium lactofermentum* AJ 12220 (FERM-P8248, FERM BP-996) resistant to methyl viologen (a superoxide producing accelerator), *Corynebacterium acetoglutamicum* AJ 12223 (FERM-P8251, FERM BP-998) resistant to puromycin (a superoxide dismutase induction inhibitor), *Brevibacterium flavum* AJ 12222 (FERM-P8250, FERM BP-997) resistant to phenylhydrazine (a superoxide radical reaction accelerator), and *Brevibacterium lactofermentum* AJ 12221 (FERM-P8249) resistant to benzoyl peroxide (an oxidizing agent which supplies oxygen for the formation of superoxide).

The mutants *Brevibacterium lactofermentum* AJ 12220, FERM P-8248, FERM BP-996, *Brevibacterium flavum* AJ 12222, FERM P-8250, FERM BP-997 and *Corynebacterium acetoglutamicum* AJ 12223, FERM P-8251, FERM BP-998 were originally deposited on May 22, 1985 at the Fermentation Research Institute, Agency of Industrial Science and Technology, Ministry of International Trade and Industry (FRI), 1- 3, Migashi 1-chome, Yatabe-machi, Tsukuba-gun, Ibaragi-ken, 305, Japan, and were accorded the FERM-P number indicated above. The mutants deposited were then converted into deposits under the Budapest Treaty on Mar. 13, 1986, and were accorded the corresponding FERM-BP numbers.

These strains may be grown to produce L-lysine by the known techniques commonly used for L-lysine fermentation.

Common culture media containing carbon sources, nitrogen sources, inorganic ions and other nutrients may be used for this purpose. As examples of carbon sources, beet and cane juices, waste molasses, starch hydrolyzate and other sugar materials; and organic acids such as acetic acid can be mentioned.

Ammonium salts, ammonia water, urea and other nitrogen sources commonly used for L-lysine fermentation may be employed. Furthermore, inorganic ions (e.g., phosphate ions and magnesium ions) and vitamins (e.g., thiamine) may also be added to culture medium as required.

For a strain which requires a definite substance for its growth (such as auxotrophic mutants), this substance should be added to the culture medium. Alternatively, protein hydrolyzate, corn steep liquor, meat extract or yeast extract containing this substance should be added to the culture medium.

Culture conditions are also the same as those commonly used for L-lysine fermentation; namely, aerobic conditions at a temperature in the range from 30° to 40° C. and at a pH in the range from 6 to 8. L-lysine can be isolated from the fermentation liquor by usual methods.

This invention is based on the new findings that the L-lysine productivity of L-lysine producing strains can be enhanced by intensifying their superoxide dismutase activity. And hence the process of this invention allows production of L-lysine at lower costs by simple techniques.

Other features of the invention will become apparent in the course of the following descriptions of exemplary embodiments which are given for illustration of the invention and are not intended to be limiting thereof.

Some examples of deriving the mutant strains of this invention are explained below.

The species given below were used as mother strains:
*Brevibacterium lactofermentum*; AJ 3990, FERM-P3387 (AEC[r1)], ML[r2)], Ala−)
*Brevibacterium flavum*; FAEC 1-30, FERM-P282 (AEC[r])
*Corynebacterium acetoglutamicum*, AJ 3792, FERM-P2650 (AEC[r], HL[r3)])
1) resistant to AEC
2) resistant to ML
3) resistant to HL Each of these mother strains was grown on a bouillon slant culture for 24 hours, followed by treatment with 250 $\mu$g/ml of N-nitro-N'-methyl-N-nitrosoguanidine at 30° C. for 20 minutes, giving mutant strains.

To a base medium containing 1 g/dl yeast extract, 1 g/dl peptone, 0.5 g/dl sodium chloride and 2 g/dl agar, the following were added separately: (1) methyl viologen (1.5 $\mu$g/ml), (2) puromycin (0.5 $\mu$g/ml), (3) phenylhydrazine (20 $\mu$g/ml), and (4) benzoyl peroxide (20 $\mu$g/ml). Each media obtained was adjusted to pH 7.0 and then sterilized at 120° C. at 15 minutes, affording four kinds of agar media.

The mutant strains obtained above were inoculated to these agar media, and incubated at 31.5° C. for 48 hours.

The colonies formed were collected, and each drug-resistant strain was given an AJ No. as shown in Table 1.

The drug-resistant strains thus obtained, as well as the mother strains, were subjected to growth test at different drug concentrations, as described below.

Each strain was incubated on a bouillon slant medium for 24 hours, and then spread on an agar plate, placed in a Petri dish 8 cm in diameter and containing 1 g/dl yeast extract, 1 g/dl peptone, 0.5 g/dl sodium chloride and 2 g/dl agar (pH: 7.0), to obtain a number of cells in the range of from $10^5$ to $10^6$ per plate. With a paper disk containing a drug at a concentration shown in Table 1 placed on each agar plate, cultivation was continued for 16 to 48 hours, and the growth condition of each strain was evaluated by the presence or absence of growth inhibition disk. The results obtained are also shown in Table 1, in which (++) represents high growth (+) moderate growth, and (−) no growth.

TABLE 1

| Drug | Strain | | |
|---|---|---|---|
| | | AJ 3990 | AJ 12220 |
| Methyl viologen | 0.1 μg/ml | ++ | ++ |
| | 0.5 μg/ml | + | ++ |
| | 1.5 μg/ml | − | ++ |
| | | AJ 3792 | AJ 12223 |
| Puromycin | 0.1 μg/ml | ++ | ++ |
| | 0.25 μg/ml | + | ++ |
| | 0.5 μg/ml | − | ++ |
| | | FAEC 1-30 | AJ 12222 |
| Phenylhydrazine | 10 μg/ml | ++ | ++ |
| | 15 μg/ml | + | ++ |
| | 20 μg/ml | − | ++ |
| | | AJ 3990 | AJ 12221 |
| Benzoyl peroxide | 5 μg/ml | ++ | ++ |
| | 10 μg/ml | + | ++ |
| | 20 μg/ml | − | ++ |

The superoxide dismutase activity of the above-mentioned drug-resistant strains and their mother strains was measured as described below. The result of measurement is summarized in Table 2.

The culture liquor of each strain (20 ml) was centrifuged for ten minutes at 10,000 rpm, the precipitate thus separated was collected, washed twice and 0.1M phosphate buffer (pH: 7) and suspended in 20 ml of the same buffer as above. The suspension was subjected to ultrasonic treatment for five minutes and then to centrifugation for 10 minutes at 10,000 rpm, and the supernatant was collected as a sample solution.

To 2.4 ml of 0.05M sodium carbonate buffer (pH: 10.2) placed in a test tube, were added 0.1 ml each of 3 mM xanthine, 3 mM EDTA, 0.15% bovine serum albumin and 0.75 mM Nitroblue tetrazonium. The sample solution prepared above (0.1 ml) was added to this reagent solution, the mixture was allowed to stand at 25° C. for ten minutes, and 0.1 ml of the xanthine oxidase solution described below was then added, followed by rapid mixing. After incubation at 25° C. for 20 minutes, 0.1 ml of 6 mM $CuCl_2$ was added to the mixture to terminate the reaction, and the absorbance at 560 nm was measured. A blank test was conducted using distilled water in place of the sample solution.

The superoxide dismutase activity that half inhibits the xanthine oxidase reaction under such measuring conditions was taken as one unit.

The xanthine oxidase solution used in the above test was prepared by diluting xanthine oxidase with 2M $(NH_4)_2SO_4$ so that the absorbance in the blank test will be approximately 0.23. The actual xanthine oxidase concentration was about $2.1 \times 10^{-7}M$.

TABLE 2

| Strain | SOD* Activity (%) |
|---|---|
| AJ 3990 | 100 |
| AJ 12220 | 147 |
| AJ 12221 | 156 |
| FAEC 1-30 | 100 |
| AJ 12222 | 127 |
| AJ 3792 | 100 |
| AJ 12223 | 139 |

*SOD: Superoxide dismutase.

The following Examples will further illustrate this invention.

EXAMPLE 1

A culture medium containing 36 mg/ml glucose, 20 mg/ml ammonium chloride, 1 mg/ml $KH_2PO_4$, 0.4 mg/ml $MgSO_4.7H_2O$, 10 μg/ml $FeSO_4.7H_2O$, 8 μg/ml $MnSO_4.7H_2O$, 1 μg/ml (as N) of acid hydrolyzate of soybean protein, 0.1 μg/ml thiamin hydrochloride and 0.3 μg/ml biotin was prepared. Thirty milliliters of this medium was dispensed in 500-ml shake flasks, sterilized by heating at 115° C. for ten minutes, and 1 g each of calcium carbonate, previously sterilized by dry heating, was further added. Each strain listed in Table 2 was innoculated to this medium, and fermentation was continued at 31.5° C. for 48 hours on a reciprocating shaker. Table 3 shows the amount of L-lysine accumulated in each fermentation liquor. As is apparent from the table, all of the drug-resistant strains tested produced L-lysine in good yields.

TABLE 3

| Strain | L-lysine HCl (g/l) | Yield based on sugar (%) |
|---|---|---|
| AJ 3990 | 13.7 | 38.1 |
| AJ 12220 | 15.4 | 42.8 |
| AJ 12221 | 15.1 | 41.9 |
| FAEC 1-30 | 5.6 | 15.6 |
| AJ 12222 | 7.7 | 21.4 |
| AJ 3792 | 10.4 | 28.9 |
| AJ 12223 | 11.3 | 31.4 |

EXAMPLE 2

A culture medium (pH: 7.0) containing 80 mg/ml (as sugar) of waste molasses, 1 mg/ml $KH_2PO_4$, 1 mg/ml $MgSO_4.7H_2O$, 1 μg/ml (as N) of acid hydrolyzate of soybean protein, and 500 mg/ml ammonium sulfate was prepared. Twenty milliliters of this medium was dispensed in 500-ml shake flasks, sterilized by steam, and 1 g each of calcium carbonate, previously sterilized by dry heating, was further added. Each strain listed in Table 4 was innoculated to this medium, and cultivation was continued at 31.5° C. for 72 hours on a reciprocating shaker. Table 4 shows the amount of L-lysine accumulated in each fermentation liquor. As is apparent from the table, all of the drug-resistant strains tested produced L-lysine in good yields.

TABLE 4

| Strain | L-lysine HCl (g/l) | Yield based on sugar (%) |
|---|---|---|
| AJ 3990 | 27.2 | 34.0 |
| AJ 12220 | 31.1 | 38.9 |
| AJ 12221 | 30.3 | 37.8 |
| FAEC 1-30 | 14.5 | 18.1 |
| AJ 12222 | 17.7 | 22.1 |

TABLE 4-continued

| Strain | L-lysine HCl (g/l) | Yield based on sugar (%) |
|---|---|---|
| AJ 3792 | 24.7 | 30.9 |
| AJ 12223 | 27.0 | 33.8 |

EXAMPLE 3

A culture medium containing 160 mg/ml (as glucose) of saccharified starch liquor, 55 mg/ml ammonium sulfate, 1 mg/ml KH$_2$PO$_4$, 0.4 mg/ml MgSO$_4$.7H$_2$O, 10 g/ml FeSO$_4$.7H$_2$O, 8 μg/ml MnSO$_4$.4H$_2$O, 1 μg/ml (as N) of acid hydrolyzate of 50 g bean protein, 0.2 μg/ml thiamin hydrochloride, 0.3 μg/ml biotin and 0.05 mg/ml of defoamer was prepared. Ten liters of this medium was charged in a 30-liter fermentor, and steam-sterilized at 115° C. for ten minutes. To this medium was added an inoculum of AJ 12221 or AJ 3990 (0.5 l), previously propagated in a separate nutritional medium, and fermentation was continued at 31.5° ±0.5° C. at an aeration rate of 0.5 l/min with agitation of 350 rpm, while maintaining the pH in the range of 6.5±0.1 with ammonia gas. The amount of L-lysine accumulated in the fermentation liquor was 76.3 g/l when AJ 12221 was used and 64.1 g/l when AJ 3990 was used.

EXAMPLE 4

A culture medium containing 80 mg/ml (as sugar) of waste molasses, 500 mg/ml ammonium sulfate, 1 mg/ml KH$_2$PO$_4$, 1 mg/ml MgSO$_4$.7H$_2$O, 2 mg/ml of acid hydrolyzed soybean protein, and 0.1 mg/ml defoamer was prepared. Ten liters of this medium was charged in a 30-liter fermentor and steam-sterilized at 120° C. for 15 minutes. To this medium was added an inoculum of AJ 12220 or AJ 3990 (0.5 l), previously propagated in a separate nutritional medium, and fermentation was carried out at 31.5° ±0.5° C. at an aeration rate of 10 l/min with agitation of 400 rpm, while maintaining the pH in the range of 6.8±0.1 with ammonia gas. After 16 hours elapsed, sterile waste molasses and defoamer were added periodically, and fermentation was continued for a total of 72 hours. The amount of L-lysine accumulated in the fermentation liquor amounted to 71 g/l when AJ 12220 was used and 56 g/l when AJ 3990 was used.

Obviously, numerous modifications and variations of the present invention are possible in light of the above teachings. It is therefore to be understood that within the scope of the appendant claims, the invention may be practiced otherwise than as specifically described herein.

What is claimed as new and desired to be secured by Letters Patent of the United States is:

1. A process for producing L-lysine, which comprises:
   i) growing in an aqueous nutrient medium containing assimilable sources of carbon, nitrogen and inorganic substances the mutant strain *Brevibacterium lactofermentum* AJ 12220 (FERM BP-996) which is (1) capable of producing L-lysine, and (2) resistant to methyl viologen at a concentration of 1.5 μg/ml; and
   ii) collecting L-lysine formed.

2. A process for producing L-lysine, which comprises:
   i) growing in an aqueous nutrient medium containing assimilable sources of carbon, nitrogen and inorganic substances the mutant strain *Corynebacterium acetoglutamicum* AJ 12223 (FERM BP-998) which is (1) capable of producing L-lysine, and (2) resistant to puromycin at a concentration of 0.5 μg/ml; and
   ii) collecting L-lysine formed.

3. A process for producing L-lysine, which comprises:
   i) growing in an aqueous nutrient medium containing assimilable sources of carbon, nitrogen and inorganic substances the mutant strain *Brevibacterium flavum* AJ 12222 (FERM BP-997) which is (1) capable of producing L-lysine, and (2) resistant to phenylhydrazine at a concentration of 20 μg/ml; and
   ii) collecting L-lysine formed.

4. A process for producing L-lysine, which comprises:
   i) growing in an aqueous nutrient medium containing assimilable sources of carbon, nitrogen and inorganic substances the mutant strain *Brevibacterium lactofermentum* AJ 12221 (FERM BP-2329) which is (1) capable of producing L-lysine, and (2) resistant to benzoyl peroxide at a concentration of 20 μg/ml; and
   ii) collecting L-lysine formed.

* * * * *